(12) United States Patent
Guglielmotti et al.

(10) Patent No.: US 8,846,745 B2
(45) Date of Patent: Sep. 30, 2014

(54) USE OF AN INDAZOLEMETHOXYALKANOIC ACID FOR REDUCING TRIGLYCERIDE, CHOLESTEROL AND GLUCOSE LEVELS

(75) Inventors: Angelo Guglielmotti, Rome (IT); Giuseppe Biondi, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 13/466,503

(22) Filed: May 8, 2012

(65) Prior Publication Data

US 2012/0283307 A1    Nov. 8, 2012

Related U.S. Application Data

(63) Continuation of application No. 12/444,442, filed as application No. PCT/EP2007/009908 on Nov. 13, 2007, now Pat. No. 8,198,310.

(30) Foreign Application Priority Data

Nov. 24, 2006 (IT) .............................. MI2006A2254

(51) Int. Cl.
*A61K 31/416*    (2006.01)

(52) U.S. Cl.
CPC .................................. *A61K 31/416* (2013.01)
USPC ........... 514/406; 514/403; 514/359; 514/183; 548/362.5; 548/361.1; 548/360.1; 548/358.1; 548/356.5

(58) Field of Classification Search
None
See application file for complete search history.

(56) References Cited

U.S. PATENT DOCUMENTS

| | | | |
|---|---|---|---|
| 5,278,183 A * | 1/1994 | Silvestrini | ...................... 514/403 |
| 6,191,158 B1 | 2/2001 | Guglielmotti et al. | |
| 6,534,534 B1 | 3/2003 | Guglielmotti et al. | |
| 8,198,310 B2 | 6/2012 | Guglielmotti et al. | |

OTHER PUBLICATIONS

"Insulin resistance in type 1 diabetes" by Greenbaum, Diabetes/Metab. Res. Rev. 18, 192-200 (2002).*
"Metabolic syndrome: maladaptation to a modern world" by Wilkin et al., J. R. Soc. Med. 97, 511-20 (2004).*
"Evidence of Islet Cell Autoimmunity in Elderly Patients With Type 2 Diabetes" by Pietropaolo et al., Diabetes 49, 32-38 (2000).*

* cited by examiner

*Primary Examiner* — Wu-Cheng Winston Shen
*Assistant Examiner* — Theodore R West
(74) *Attorney, Agent, or Firm* — Oblon, Spivak, McClelland, Maier & Neustadt, L.L.P.

(57) ABSTRACT

A method of treating insulin resistance, obesity and metabolic syndrome by administering an indazolemethoxyalkanoic acid as described herein.

6 Claims, 4 Drawing Sheets

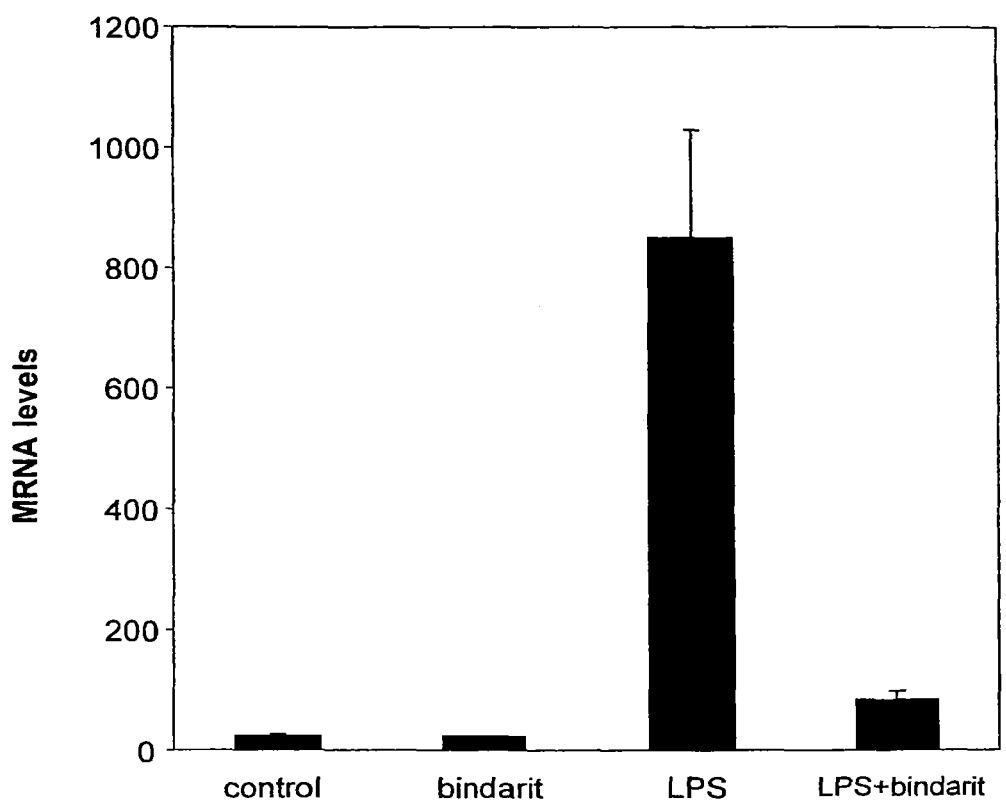

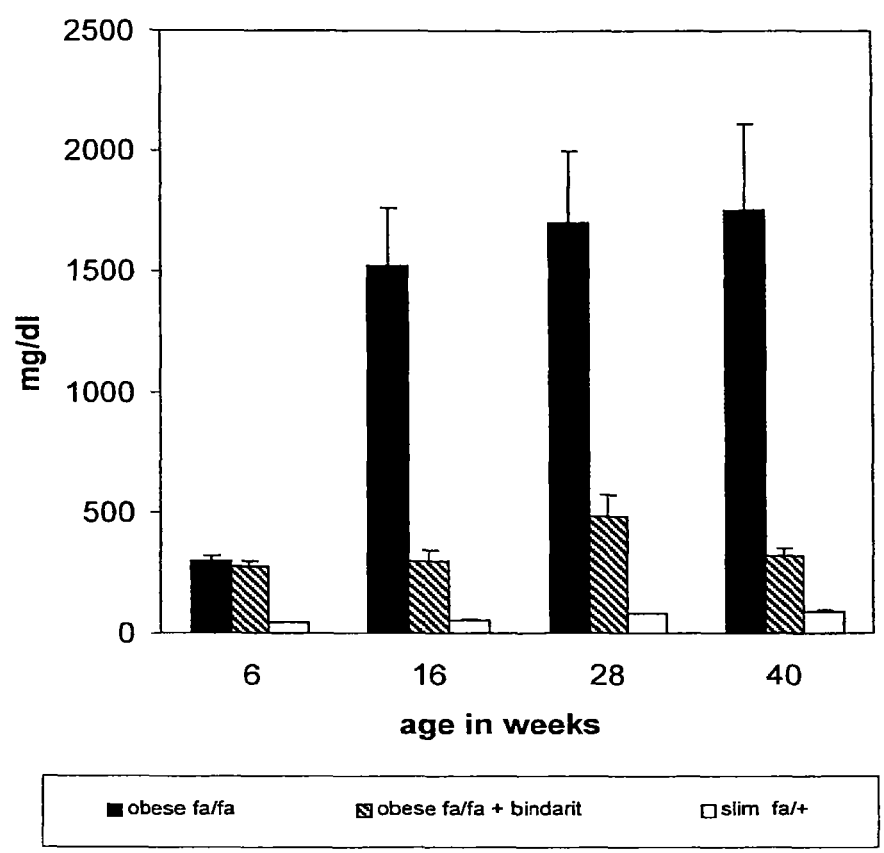

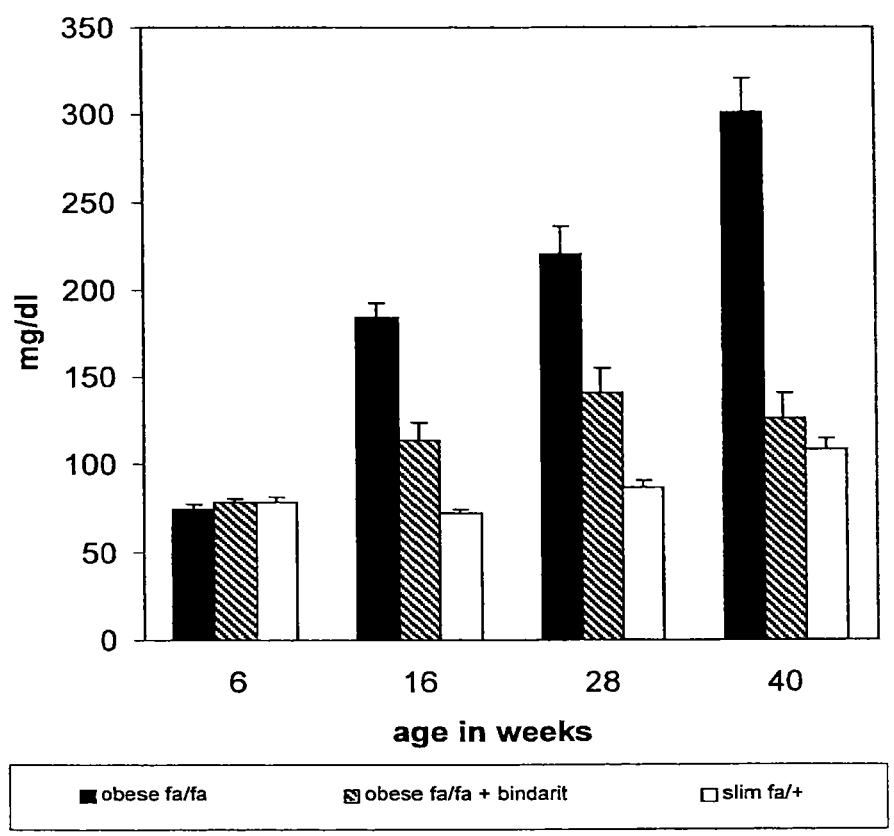

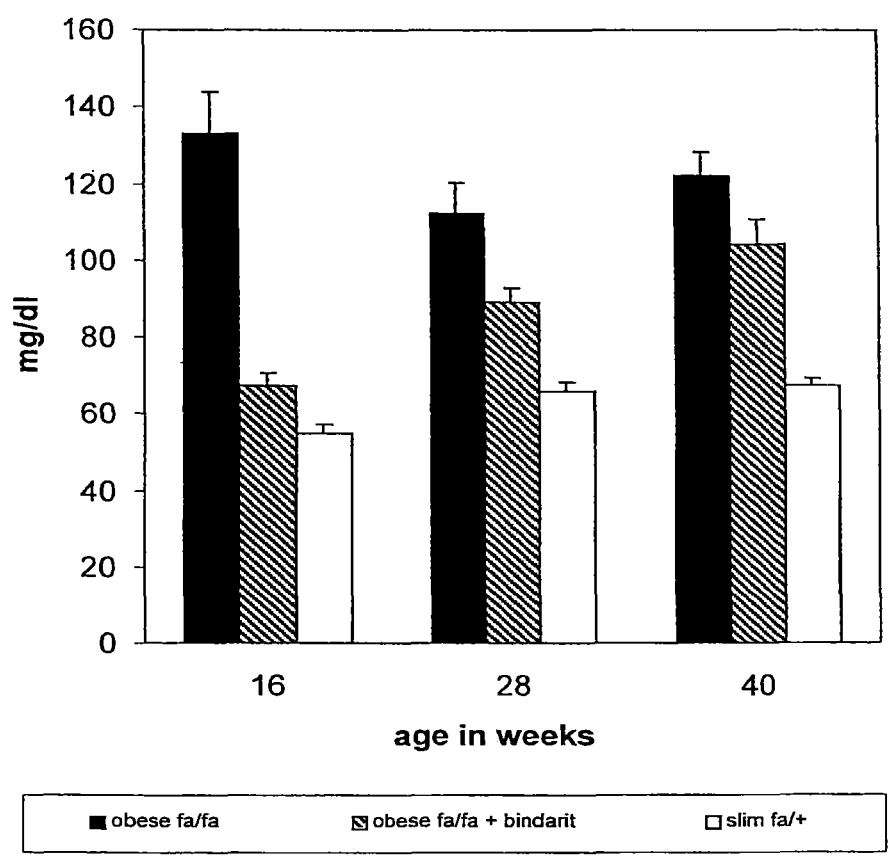

USE OF AN INDAZOLEMETHOXYALKANOIC ACID FOR REDUCING TRIGLYCERIDE, CHOLESTEROL AND GLUCOSE LEVELS

CROSS REFERENCE TO PRIOR APPLICATIONS

This is a Continuation of U.S. application Ser. No. 12/444,442, filed Apr. 23, 2009, which is a U.S. National Phase application under 35 U.S.C. §371 of International Patent Application No. PCT/EP2007/009908, filed Nov. 13, 2007, and claims the benefit of Italian Patent Application No. MI2006A002254, filed Nov. 24, 2006, both of which are incorporated by reference herein. The International Application published in English on May 29, 2008 as WO 008/061671 under PCT Article 21(2).

FIELD OF THE INVENTION

The present invention relates to the use of an indazolemethoxy-alkanoic acid to prepare a pharmaceutical composition for reducing the blood triglyceride, cholesterol and/or glucose levels.

PRIOR ART

Document EP-B1-0 382 276 describes a compound of formula (I):

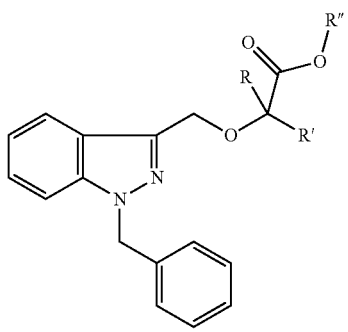

(I)

in which
R and R', which may be the same or different, are H or $C_{1-5}$ alkyl, and
R" is H or $C_{1-4}$ alkyl,
optionally, when R" is H, in the form of a salt thereof with a pharmaceutically acceptable organic or mineral base.

The abovementioned document also points out that the compound of formula (I) has analgesic activity.

For the sake of brevity, the abovementioned compound of formula (I) in which R, R' and R" have the abovementioned meanings will be referred to hereinbelow as the compound of formula (I). Thus, in the course of the present description, the expression "compound of formula (I) in which R and R', which may be the same or different, are H or $C_{1-5}$ alkyl, and R" is H or $C_{1-4}$ alkyl, optionally, when R" is H, in the form of a salt thereof with a pharmaceutically acceptable organic or mineral base" and the expression "compound of formula (I)" are equivalent.

Document EP-B1-0 510 748 describes the use of a compound of formula (I) to prepare a drug that is active in the treatment of autoimmune diseases.

In addition, document EP-B1-0 858 337 describes a pharmaceutical composition comprising a compound of formula (I) in which R=R'=$CH_3$ and R"=H, and an immunosuppressant.

Finally, document EP-B1-1 005 332 reports that the compound of formula (I) reduces the production of the protein MCP-1. More particularly, the said document describes the use of a compound of formula (I) to prepare a pharmaceutical composition for treating a disease chosen from the group comprising atherosclerosis, interstitial lung diseases, and post-operative complications in heart surgery, transplants, organ or tissue replacements, or prosthesis implants.

SUMMARY OF THE INVENTION

It has now been found, surprisingly, that the compound of formula (I) reduces the blood triglyceride, cholesterol and glucose levels.

The reason for this activity has not yet been entirely elucidated, but, without thereby wishing to limit the present invention, it is thought that this could be related to the capacity of the compound of formula (I) to inhibit the expression of IL-12.

As is known, IL-12 is a cytokine produced by monocytes, macrophages, neutrophils, dendritic cells and antibody-producing B cells, and also by keratinocytes and a number of tumoral cell lines (epidermoid carcinoma).

IL-12 modulates the activation of the "natural killer" (NK) cells and T cells, and the induction of interferon-gamma (IFN-γ), which is a cytokine that participates in regulating the immune response.

BRIEF DESCRIPTION OF THE FIGURES

FIG. 1: Demonstration that Bindarit is capable of significantly inhibiting the expression of LPS-induced IL-12 in human monocytes, reducing the levels of specific mRNA by about 100-fold.

FIG. 2: Demonstration that the administration of bindarit induces a significant reduction in the circulating levels of triglycerides and cholesterol.

FIG. 3: Demonstration that the administration of bindarit induces a significant reduction in the circulating levels of triglycerides and cholesterol.

FIG. 4: Demonstration that, as a consequence of the glucose intolerance and the insulin resistance characteristic of the strain of rats used, the obese animals show an increase in glycaemia. The treatment with bindarit induces a significant reduction in the glycemia.

DETAILED DESCRIPTION OF THE INVENTION

In a first aspect, the present invention relates to the use of a compound of formula (I):

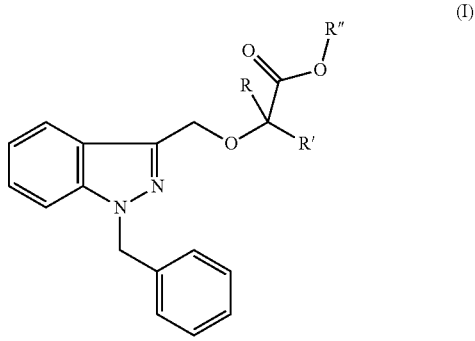

(I)

in which

R and R', which may be the same or different, are H or $C_{1-5}$ alkyl, and

R" is H or $C_{1-4}$ alkyl, optionally, when R" is H, in the form of a salt thereof with a pharmaceutically acceptable organic or mineral base, to prepare a pharmaceutical composition for reducing the blood triglyceride, cholesterol and glucose levels.

In a second aspect, the present invention relates to a method of treatment for reducing the blood triglyceride, cholesterol and/or glucose levels in a human patient in whom the blood triglyceride, cholesterol and/or glucose levels are higher than normal, the said method comprising the administration of an effective dose of a compound of formula (I):

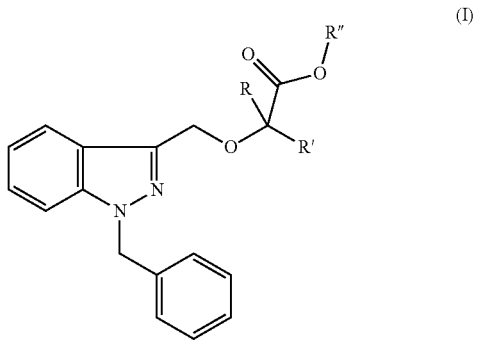

in which

R and R', which may be the same or different, are H or $C_{1-5}$ alkyl, and

R" is H or $C_{1-4}$ alkyl, optionally, when R" is H, in the form of a salt thereof with a pharmaceutically acceptable organic or mineral base.

A preferred compound of formula (I) is that in which R" is H and R=R'=$CH_3$. This compound is known as "bindarit".

By virtue of their capacity to normalize the blood triglyceride, cholesterol and glucose levels, the pharmaceutical compositions and, respectively, the method of treatment according to the present invention will be useful for treating diseases or pathological conditions such as, for example, obesity, metabolic syndrome, cardiovascular diseases, diabetes, insulin resistance and cancer.

Obesity may be considered as a chronic pathological condition resulting from complex interactions between cultural, psychological and genetic factors. In the last thirty years, there has been a great increase in interest in the pharmacological control of obesity and related health problems, moreover on account of the social costs associated with this condition. Much evidence has demonstrated that being overweight or obese substantially increases the risk of death caused by various conditions including diabetes, hypertension, dyslipidaemia, coronary cardiopathies, congestive heart insufficiency, myocardial infection, and even certain of forms of cancer. In addition, a higher body weight is also associated with increased mortality in general.

Obesity and insulin resistance share a complex relationship that leads to the development of various types of metabolic disorder, including type-2 diabetes. The adipocytes accumulate triglycerides and release free fatty acids, which are cholesterol precursors, that can play an important role in the development and progression of diabetes and its associated disorders.

High levels of circulating lipids may be the consequence of various pathological conditions or, in turn, may be the cause of specific diseases.

Disorders commonly related with high levels of lipids (hyperlipidaemia) include cardiovascular diseases or conditions including coronary disorders, hypertension, thrombosis, ischaemic events, for instance infarction, strokes and organ insufficiency.

In addition, for certain individuals, the simultaneous presence of the symptoms described above, which include hypertension, hyperlipidaemia and obesity, may indicate a particular predisposition to diabetes and to cardiovascular disorders, a condition currently indicated as metabolic syndrome.

In recent decades, the prevalence of obesity and related disorders has increased exponentially, reaching epidemic proportions in the United States and Europe. Recent estimates suggest that, despite the continued efforts made by the public health organizations, the health problems of obese and overweight individuals will continue to increase.

Consequently, the targeted and effective treatment of obesity is a primary objective of the pharmaceutical industry.

Preferably, the pharmaceutical compositions of the present invention are prepared in suitable dosage forms comprising an effective dose of at least one compound of formula (I) and at least one pharmaceutically acceptable inert ingredient.

Examples of suitable dosage forms are tablets, capsules, coated tablets, granules, solutions and syrups for oral administration; medicated plasters, pastes, creams and ointments for transdermal administration; suppositories for rectal administration and sterile solutions for administration via the injection or aerosol route.

Other examples of suitable dosage forms are those with sustained release and based on liposomes for administration via either the oral or injection route.

The dosage forms may also contain other conventional ingredients, for instance preserving agents, stabilizers, surfactants, buffers, osmotic pressure-regulating salts, emulsifiers, sweeteners, colorants, flavourings and the like.

In addition, when required for particular therapies, the pharmaceutical composition according to the present invention may also contain other pharmacologically active ingredients whose simultaneous administration is useful.

The amount of compound of formula (I) in the pharmaceutical composition according to the present invention may vary within a wide range as a function of known factors, for instance the type of disease to be treated, the severity of the disease, the body weight of the patient, the dosage form, the selected route of administration, the number of daily administrations and the efficacy of the selected compound of formula (I). However, a person skilled in the art may determine the optimum amount in a simple and routine manner.

Typically, the amount of compound of formula (I) in the pharmaceutical composition according to the present invention will be such that it provides a level of administration of between 0.0001 and 100 mg/kg/day. Preferably, the level of administration is between 0.05 and 50 mg/kg/day and even more preferably between 0.1 and 10 mg/kg/day.

The dosage forms of the pharmaceutical composition according to the present invention may be prepared according to techniques that are well known to pharmaceutical chemists, including mixing, granulation, compression, dissolution, sterilization and the like.

The activity of the compound of formula (I) was evaluated in vitro in human monocytes by means of gene expression analysis techniques using "GeneChip" and in vivo in Zucker rats, an experimental model of type-2 diabetes characterized by glucose intolerance and insulin resistance accompanied by hyperglycaemia and hyperlipidaemia.

As is known to those skilled in the art, the above-mentioned experimental models are predictive of activity in man.

Test 1

Analysis of the Gene Expression in Human Monocytes (GeneChip Technology)

The capacity of bindarit to inhibit the expression of IL-12 by human monocytes stimulated with lipopolysaccharide (LPS) was evaluated.

Human monocytes were used, which were isolated from healthy donors by centrifugation on a Ficoll gradient and purified by two successive centrifugation steps, followed by a step of isolation by means of an immunomagnetic system of negative cell separation (MACS, Miltenyi Biotech), using specific antibodies.

The cells were stimulated with LPS (100 ng/ml) for 4 hours in the presence or absence of bindarit (300 μM). The product was tested in the form of the sodium salt obtained by salification with equimolar sodium hydroxide and subsequent dilution in the medium used. The total RNA was extracted from cells using TRizol (Invitrogen Life Technologies) according to manufacturer's instructions, reverse-transcribed and prepared by GeneChip hybridization.

As shown by the results obtained given in FIG. 1, bindarit is capable of significantly inhibiting the expression of LPS-induced IL-12 in human monocytes, reducing the levels of specific mRNA by about 100-fold.

Similar results were obtained using bindarit in acid form dissolved in DMSO.

Test 2

Effect of Bindarit on Circulating Levels of Triglycerides, Cholesterol and Glucose in Zucker Rats The activity of bindarit was tested in an experimental model in rats.

The study was performed on rats 5 weeks old on arrival, of the Zucker strain homozygous for the "fa" allele (fa/fa), insulin-resistant, hyperinsulinaemic and obese, and on rats of the same age of the heterozygous Zucker control strain (fa/+), phenotypically normal, insulin-sensitive and slim.

At six weeks old, the obese Zucker rats were divided into two groups, one of which was fed with a standard rodent diet, and the other with a standard rodent diet supplemented with 0.5% bindarit.

The slim Zucker rats of the same age were used as controls and fed with a standard rodent diet.

Blood samples were taken from the animals periodically (at 6, 16, 28 and 40 weeks old) for enzymatic measurement of the circulating levels of triglycerides, cholesterol and glucose.

The results are illustrated in FIGS. 2, 3 and 4.

FIGS. 2 and 3 show that the administration of bindarit induces a significant reduction in the circulating levels of triglycerides and cholesterol.

FIG. 4 shows that, as a consequence of the glucose intolerance and the insulin resistance characteristic of the strain of rats used, the obese animals show an increase in glycaemia. The treatment with bindarit induces a significant reduction in the glycaemia.

The diabetic syndrome characteristic of the obese Zucker rats shows many similarities with human type-2 diabetes and is also accompanied by appreciable hyperlipidaemia.

The following examples of pharmaceutical compositions are given to illustrate the invention in greater detail without, however, limiting it.

EXAMPLE 1

| Tablets | |
|---|---|
| Each tablet contains: | |
| a) Active substance: | |
| Bindarit | 300 mg |
| b) Excipients: | |
| Microcrystalline cellulose | 66 mg |
| Corn starch | 50 mg |
| Sodium starch glycolate | 19 mg |
| Povidone | 18 mg |
| Colloidal silicon dioxide | 14.5 mg |
| Magnesium stearate | 4.5 mg |

EXAMPLE 2

| Liposomes for administration via the oral and/or injection route | |
|---|---|
| a) Active substance: | |
| Bindarit | 4 mg/ml |
| b) Liposome composition (w/w %): | |
| Phosphatidylcholine | 94 |
| Lysophosphatidylcholine | 3 |
| N-Acylethanolamine | 1 |
| Phosphatidylethanolamine | 0.1 |
| Triglycerides | 1 |
| Free fatty acids | 0.75 |
| DL-α-tocopherol | 0.15 |

EXAMPLE 3

| Granulate | |
|---|---|
| Formula A | |
| Each sachet contains: | |
| a) Active substance: | |
| Bindarit | 300 mg |
| b) Excipients: | |
| Trometamol | 230 mg |
| Maltitol | 1850 mg |
| Mannitol | 1600 mg |
| K-Acesulfame | 30 mg |
| Sucralose | 30 mg |
| Flavourings | 100 mg |
| Formula B | |
| Each sachet contains: | |
| a) Active substance: | |
| Bindarit sodium salt (equal to 300 mg of free acid) | 309.25 mg |

-continued

| Granulate | |
|---|---|
| b) Excipients: | |
| Potassium bicarbonate | 300 mg |
| Sucrose | 2500 mg |
| Flavourings | 70 mg |
| K-Acesulfame | 50 mg |
| Aspartame | 20 mg |

EXAMPLE 4

| Oral drops | |
|---|---|
| a) Active substance: | |
| Bindarit | 20 g |
| b) Excipients: | |
| Potassium hydroxide | 7 g |
| Sucrose | 20 g |
| Sucralose | 0.5 g |
| Polysorbate-20 | 0.2 g |
| Methyl p-hydroxybenzoate | 0.018 g |
| Propyl p-hydroxybenzoate | 0.011 g |
| Disodium edetate | 0.01 g |
| Glycerol | 15 g |
| Flavourings | 6 g |
| Purified water | qs 100 ml |

EXAMPLE 5

| Injectable solutions | |
|---|---|
| Each vial contains: | |
| a) Active substance: | |
| Bindarit | 0.3 g |
| b) Excipients: | |
| Trometamol | 0.24 g |
| Poloxamer | 0.01 g |
| Sodium edetate | 0.001 g |
| Water for injection | qs 10 ml |

The invention claimed is:

1. A method for reducing blood glucose levels in a patient suffering from type-2 diabetes, comprising administering, to a patient in need thereof, an effective amount of a compound of formula (I):

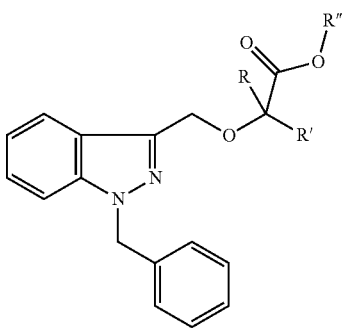

wherein
R and R', which may be the same or different, are H or $C_{1-5}$ alkyl, and
R" is H or $C_{1-4}$ alkyl,
or a pharmaceutically acceptable salt thereof.

2. A method according to claim 1, wherein R" is H and R and R' are both $CH_3$.

3. A method according to claim 1, which comprises administration of

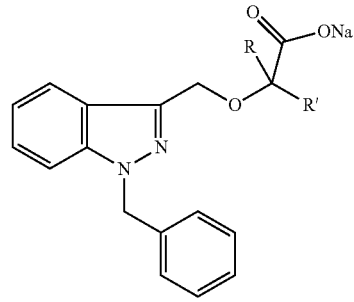

wherein R and R' are both $CH_3$.

4. A method according to claim 1, which comprises administering said compound of formula (I) or pharmaceutically acceptable salt thereof in an amount of 0.0001 to 100 mg/kg/day.

5. A method according to claim 1, which comprises administering said compound of formula (I) or pharmaceutically acceptable salt thereof in an amount of 0.05 to 50 mg/kg/day.

6. A method according to claim 1, which comprises administering said compound of formula (I) or pharmaceutically acceptable salt thereof in an amount of 0.1 to 10 mg/kg/day.

* * * * *